United States Patent
Omoto et al.

(10) Patent No.: US 10,653,296 B2
(45) Date of Patent: May 19, 2020

(54) INSERTION DEVICE

(71) Applicant: OLYMPUS CORPORATION, Tokyo (JP)

(72) Inventors: Keijiro Omoto, Hachioji (JP); Yasuaki Natori, Akishima (JP); Takashi Suzuki, Hino (JP); Yoshitaka Umemoto, Hachioji (JP); Takashi Yamashita, Hachioji (JP); Fumiyuki Onoda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 319 days.

(21) Appl. No.: 15/670,508

(22) Filed: Aug. 7, 2017

(65) Prior Publication Data

US 2017/0332883 A1    Nov. 23, 2017

Related U.S. Application Data

(63) Continuation of application No. PCT/JP2016/077458, filed on Sep. 16, 2016.

(30) Foreign Application Priority Data

Oct. 27, 2015    (JP) ................................. 2015-211135

(51) Int. Cl.
*A61B 1/00* (2006.01)
*G02B 23/24* (2006.01)

(52) U.S. Cl.
CPC ...... *A61B 1/00071* (2013.01); *A61B 1/00006* (2013.01); *A61B 1/0016* (2013.01); *A61B 1/00039* (2013.01); *A61B 1/00078* (2013.01); *A61B 1/00156* (2013.01); *G02B 23/2476* (2013.01)

(58) Field of Classification Search
CPC ............ A61B 1/00071; A61B 1/00006; A61B 1/00156; A61B 1/0016
See application file for complete search history.

(56) References Cited

U.S. PATENT DOCUMENTS

| 5,482,029 A | * | 1/1996 | Sekiguchi | ........ A61B 1/00039 |
| | | | | 600/109 |
| 5,810,715 A | * | 9/1998 | Moriyama | ........ A61B 1/00078 |
| | | | | 600/139 |
| 5,989,230 A | * | 11/1999 | Frassica | ................ A61F 2/0009 |
| | | | | 600/109 |

(Continued)

FOREIGN PATENT DOCUMENTS

| EP | 1 908 389 A1 | 4/2008 |
| JP | 2001-170000 A | 6/2001 |

(Continued)

OTHER PUBLICATIONS

Extended Supplementary European Search Report dated Sep. 3, 2018 in European Patent Application No. 16 85 9435.6.

(Continued)

*Primary Examiner* — Matthew J Kasztejna
(74) *Attorney, Agent, or Firm* — Scully, Scott, Murphy & Presser, P.C.

(57) ABSTRACT

An insertion device includes a thin and elongated insertion section, a rotating body which is rotated to advance or retreat the insertion section, a driving force supply source which supplies a driving force to the rotating body, a variable stiffness section provided for the insertion section and permitting stiffness of the insertion section to be varied, a stiffness detector which detects the stiffness of the insertion section varied by the variable stiffness section, and a controller which controls the driving force supply source in accordance with the stiffness of the insertion section detected by the stiffness detector.

4 Claims, 9 Drawing Sheets

(56) References Cited

U.S. PATENT DOCUMENTS

| | | | |
|---|---|---|---|
| 8,747,300 B2* | 6/2014 | Frassica | A61B 17/12099 600/112 |
| 2004/0186368 A1* | 9/2004 | Ramzipoor | A61B 1/00082 600/407 |
| 2006/0149130 A1 | 7/2006 | Konstantin et al. | |
| 2008/0262305 A1* | 10/2008 | Omoto | A61B 1/00006 600/118 |
| 2016/0150945 A1 | 6/2016 | Okamoto | |

FOREIGN PATENT DOCUMENTS

| | | | |
|---|---|---|---|
| JP | 2004-188217 A | | 7/2004 |
| JP | 2009018116 | * | 1/2009 |
| JP | 2014-004268 A | | 1/2014 |
| JP | 5750622 B1 | | 7/2015 |
| WO | WO 2015/072233 A1 | | 5/2015 |

OTHER PUBLICATIONS

Chinese Office Action dated Nov. 8, 2018 in Chinese Patent Application No. 201680006056.5.
Chinese Office Action dated Jun. 5, 2018 in Chinese Patent Application No. 201680006056.5.
International Search Report dated Nov. 1, 2016 issued in PCT/JP2016/077458.
English translation of International Preliminary Report on Patentability dated May 11, 2018 together with the Written Opinion received in related International Application No. PCT/JP2016/077458.

* cited by examiner

| Rotation amount | Output potentiometer | Index current | Correction current |
|---|---|---|---|
| 1 | Ra | IA | Δia |
| 2 | Rb | IB | Δib |
| 3 | Rc | IC | Δic |

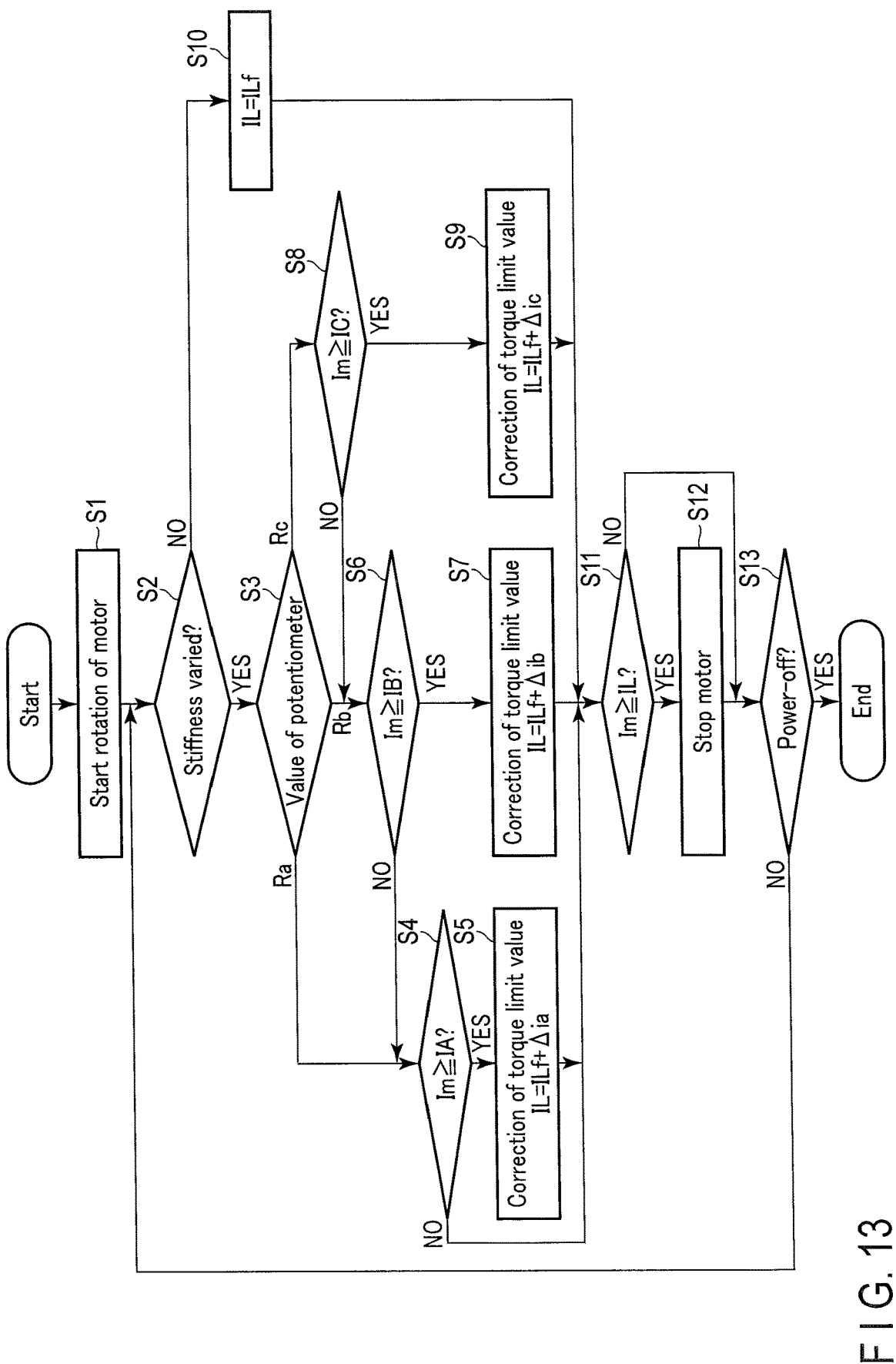
F I G. 13

INSERTION DEVICE

CROSS-REFERENCE TO RELATED APPLICATIONS

This application is a Continuation Application of PCT Application No. PCT/JP2016/077458, filed Sep. 16, 2016 and based upon and claiming the benefit of priority from the prior Japanese Patent Application No. 2015-211135, filed Oct. 27, 2015, the entire contents of both of which are incorporated herein by reference.

BACKGROUND OF THE INVENTION

1. Field of the Invention

The present invention relates to a self-propelled insertion device.

2. Description of the Related Art

In general, the insertion device of an endoscope or the like is inserted into a body cavity. As this type of insertion device, a self-propelled insertion device known in the art, in which a rotating body serving as an insertion assisting tool is provided for an insertion section, for example. In this type of insertion device, the rotating body is rotated to generate a propulsion force with which the insertion section is advanced or retreated, and the operator's operation of inserting the insertion section is assisted thereby. An insertion device provided with this type of insertion assisting tool is propose, for example, in Jpn. Pat. Appln. KOKAI Publication No. 2014-004268.

Where an insertion section is inserted into a body portion having complicated flexures, like the large intestine, the insertion section bends more when it is inserted into a deeper portion, and the insertion force applied from the proximal portion may not be transmitted to the distal end. To solve this problem, for example, Jpn. Pat. Appln. KOKAI Publication No. 2004-188217 discloses a mechanism for increasing the stiffness of an insertion section. Since the bend of the insertion section is corrected thereby, easy insertion of the insertion section is assisted.

BRIEF SUMMARY OF THE INVENTION

An insertion device according to an aspect of the invention comprises: a thin and elongated insertion section; a rotating body which is rotated to advance or retreat the insertion section; a driving force supply source which supplies a driving force to the rotating body; a variable stiffness section provided for the insertion section and permitting stiffness of the insertion section to be varied; a stiffness detector which detects the stiffness of the insertion section varied by the variable stiffness section; and a controller which controls the driving force supply source in accordance with the stiffness of the insertion section detected by the stiffness detector.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 13 is a flowchart illustrating the processing of a torque limit function.

DETAILED DESCRIPTION OF THE INVENTION

Figure 1:
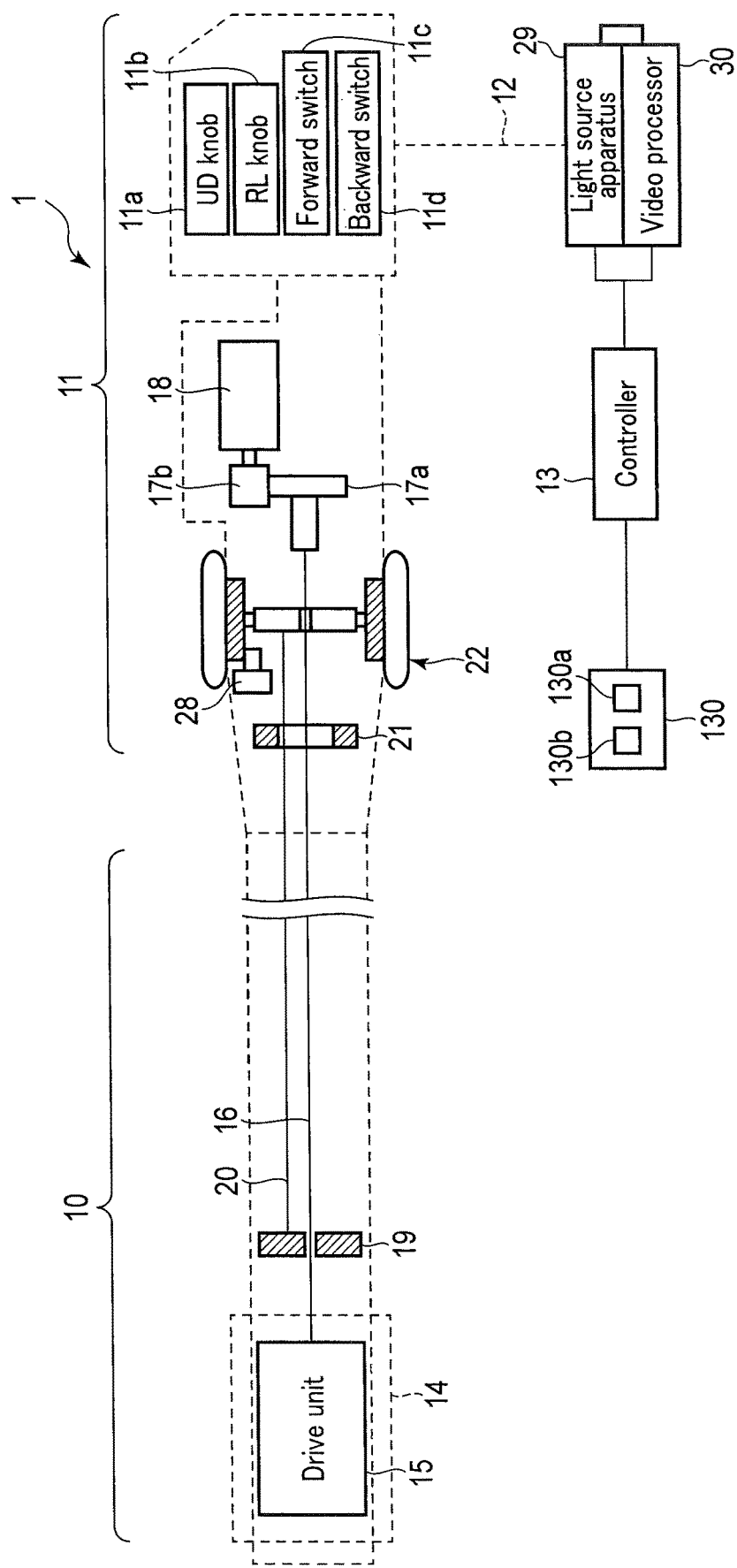
FIG. 1 is a diagram illustrating the structure of an endoscope system, which is an example of an insertion device according to one embodiment of the present invention.

Embodiments of the present invention will now be described with reference to the accompanying drawings. FIG. 1 is a diagram illustrating the structure of an endoscope system, which is an example of an insertion device according to one embodiment of the present invention. The endoscope system includes an endoscope 1. The endoscope 1 includes an insertion section 10 and an operation unit 11. The insertion section 10 is thin and elongated, and is configured to be inserted into a living body. The operation unit 11 is at the proximal end of the insertion section 10. The operation unit 11 is connected via a light source apparatus 29 to a controller 13 by means of a universal cord 12. In the description set forth below, the side where the distal end of the insertion section 10 is located will be referred to as a distal side, and the side where the operation unit 11 is located will be referred to as a proximal side.

The insertion section includes a distal end portion and a bendable portion. The distal end portion is located at the distal end of the insertion section 10 and cannot be bent. The distal end portion contains an imaging element inside. The imaging element generates a video signal based on an object image on the distal side of the insertion section 10. The video signal generated by the imaging element is transmitted to the light source apparatus 29 through a signal line (not shown) passing through both the insertion section 10 and the universal cord 12, and further to the controller 13. The bendable portion is a portion formed on the proximal side of the distal end portion. The bendable portion includes a portion which is actively bent in response to the operation of an UD knob 11a or an RL knob 11b provided on the operation unit 11.

A spiral tube 14 is fitted on the insertion section 10. The spiral tube 14 is a tubular rotating body made of a soft material such as rubber. A spiral fin is provided on the outer circumferential face of the spiral tube 14 and extends along the longitudinal axis. The spiral tube 14 is in contact with the drive unit 15 inside the insertion section 10, with the coating of the insertion section 10 therebetween. The drive unit 15 is connected to one end of the drive shaft 16. A motor 18, serving as a driving force supply source, is connected to the other end of the drive shaft 16 by means of gears 17a and 17b. An encoder is provided in the neighborhood of the motor 18. The encoder changes the rotation amount of the motor 18 into a rotation signal, and this rotation signal is supplied to the controller 13 via the light source apparatus 29 by means of the universal cord 12.

Inside the insertion section 10, a front ferrule 19 is provided in the neighborhood of the spiral tube 14, and this ferrule 19 has an opening through which the drive shaft 16 is inserted. A wire 20 is attached to the front ferrule 19. A plurality of coil pipes (not shown) are arranged in the longitudinal direction of the wire 20. The wire 20 passes through a rear ferrule 21 (which has an opening through which the drive shaft 16 and the wire 20 are inserted) and is attached to the variable stiffness section 22. The variable stiffness section 22 will be detailed later.

The controller 13 is a control unit made of ASIC. For example, the controller 13 controls the driving power of the motor 18 in such a manner as to advance the insertion section 10 in response to the operation of a forward switch 11c of the operation unit 11 or the operation of pedal 130a of a foot switch 130, and also controls the driving power of the motor 18 in such a manner as to retreat the insertion section 10 in response to the operation of the backward switch 11d of the operation unit 11 or the operation of pedal 130b of the foot switch 130. The advance of the insertion section 10 is a movement of the insertion section 10 in the distal direction. The retreat of the insertion section 10 is a movement of the insertion section 10 in the proximal direction. The controller 13 receives a rotation signal from the encoder arranged in the neighborhood of the motor 18, and controls the driving power of the motor 18 such that the motor 18 rotates by a preset rotation amount based on the rotation signal. If the torque of the motor 18 exceeds a predetermined torque limit value, then the controller 13 stops supplying the driving power to the motor 18. Various images based on video signals from the insertion section 10 are supplied to a video processor 30 via the light source apparatus 29 connected to the universal cord 12, and are displayed on a monitor (not shown).

The foot switch 130 is connected to the controller 13. The foot switch 130 includes a pedal stepped on by the operator and supplies an instruction signal corresponding to an operation amount of the pedal to the controller 13. For example, when the right-foot pedal 130a is stepped on, the foot switch 130 generates an instruction signal for advancing the spiral tube 14. When the left-foot pedal 130b is stepped on, the foot switch 130 generates an instruction signal for retreating the spiral tube 14.

Figure 2:
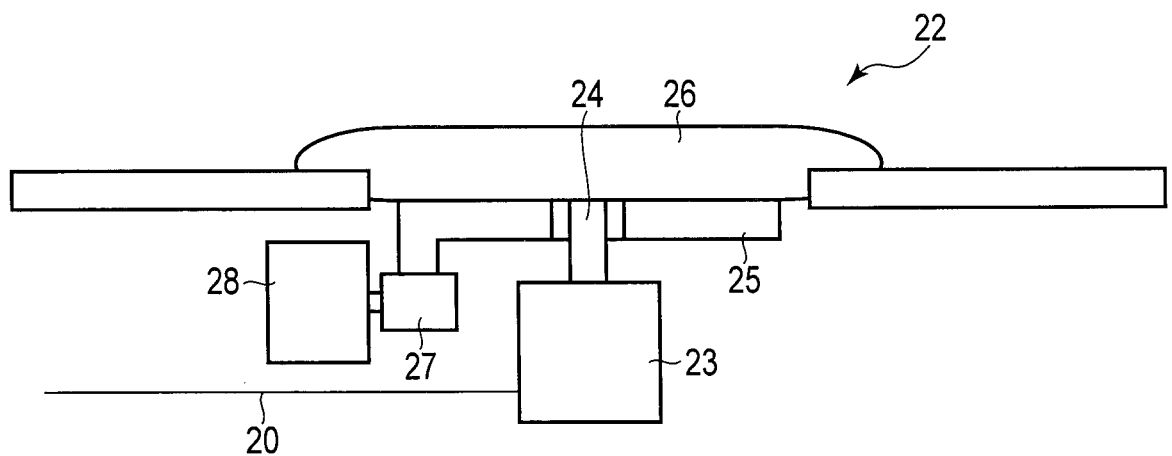
FIG. 2 is a diagram illustrating a first example of a variable stiffness section.

FIG. 2 is a diagram illustrating a first example of the variable stiffness section 22. As shown in FIG. 2, the wire 20 is attached to a movement ring 23. A pin 24 is attached to the movement ring 23. A cam ring 25 includes a gentle cam groove (not shown). The cam ring 25 is attached to a stiffness varying ring 26. The pin 24 extends in a direction perpendicular to the longitudinal direction of the insertion section 10 and is attached to the cam groove of the cam ring 25. The stiffness varying ring 26 is an operation section that can be rotated by the operator. When the stiffness varying ring 26 is rotated, the cam ring 25 is rotated thereby, and the pin 24 moves along the cam shape of the cam ring 25. As a result, the movement ring 23 is vertically moved.

The cam ring 25 is provided with inner teeth, and a gear 27 that is rotatable around the longitudinal axis of the insertion section 10 in accordance with the rotation of the cam ring 25 is in mesh with the inner teeth. The gear 27 is assembled with a potentiometer 28 serving as a stiffness detector.

Figure 3A:
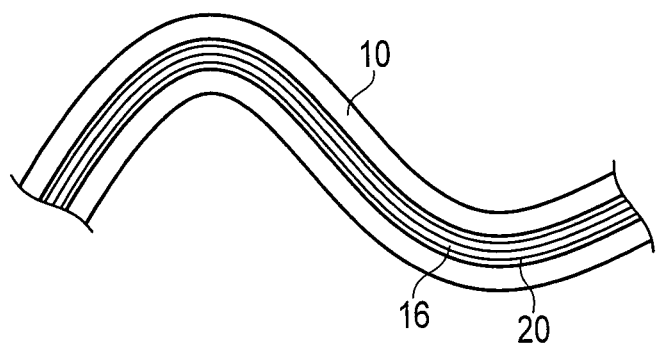
FIG. 3A illustrates an example of stiffness variation.
Figure 3B:
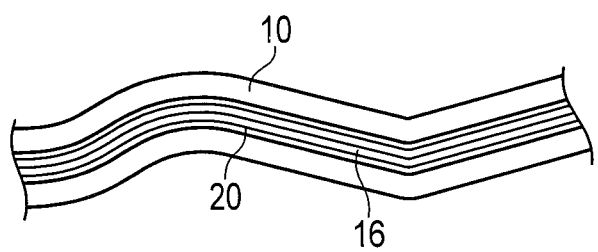
FIG. 3B illustrates an example of stiffness variation.

With the structure shown in FIG. 2, when the operator rotates the stiffness varying ring 26, the pin 24 moves along the cam groove of the cam ring 25 attached to the stiffness varying ring 26, in accordance with the rotation of the stiffness varying ring 26. At the time, the movement ring 23 is vertically moved in accordance with the movement of the pin 24. When the movement ring 23 is vertically moved, the wire 20 is pushed or pulled, and a coil pipe connected to the wire 20 is expanded or contracted. For example, when the stiffness varying ring 26 is rotated in the direction in which the wire 20 is pushed, the coil pipe is expanded. In this state, the insertion section 10 and the drive shaft 16 incorporated therein can be easily bent, as shown in FIG. 3A. On the other hand, when the stiffness varying ring 26 is rotated in the direction in which the wire 20 is pulled, the coil pipe is contracted. In this state, the insertion section 10 and the drive shaft 16 incorporated therein cannot be easily bent, as shown in FIG. 3B. In the following, the state shown in FIG. 3A will be referred to as the state in which the stiffness of the insertion section 10 is varied, and the state shown in FIG. 3B will be referred to as the state in which the stiffness of the insertion section 10 is not varied.

Figure 4:
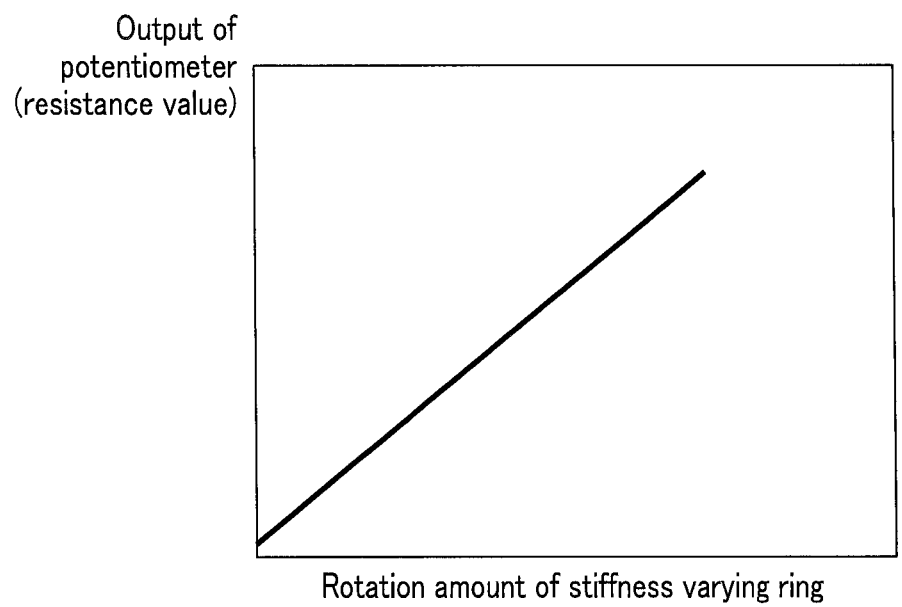
FIG. 4 is a graph representing the relationship between the rotation amount of a stiffness varying ring and the output value of a potentiometer.

When the stiffness varying ring 26 is rotated, the cam ring 25 in mesh with the stiffness varying ring 26 is also rotated. The rotation of the cam ring 25 is transmitted to the potentiometer 28 via the gear 27. The potentiometer 28 is a rotation-type potentiometer and is configured to change the resistance value in accordance with the rotation of the gear 27. For example, assuming that the resistance value of the potentiometer 28 is a minimum value when the stiffness varying ring is least rotated, the rotation amount of the stiffness varying ring 26 and the resistance value of the potentiometer 28 change substantially in proportion to each other, as shown FIG. 4. Therefore, by associating the rotation amount of the stiffness varying ring 26 and the degree of stiffness of the insertion section 10 with each other in advance, the degree of stiffness can be detected based on an output of the potentiometer 28.

Figure 5:
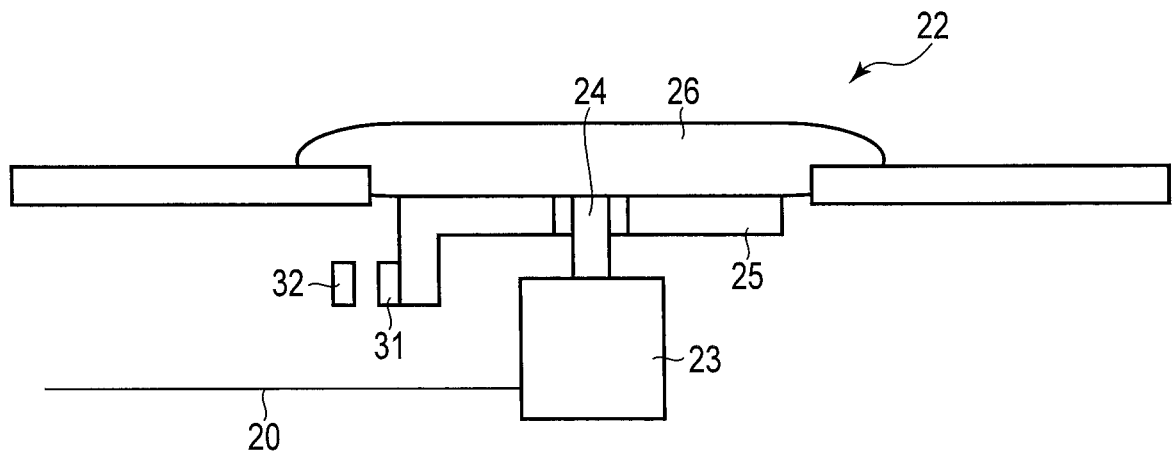
FIG. 5 is a diagram illustrating a second example of a variable stiffness section.

The structure of the variable stiffness section 22 can be modified in various ways. For example, FIG. 5 shows a variable stiffness section 22 in which the structure of the stiffness detector is modified. In FIG. 5, the same reference symbols as used in FIG. 2 denote similar structural elements to those of FIG. 2. A magnet 31 is attached to the side face of the cam ring 25 shown in FIG. 5. A hall sensor 32 is arranged such that it can detect a magnetic flux generated by the magnet 31.

Figure 6:
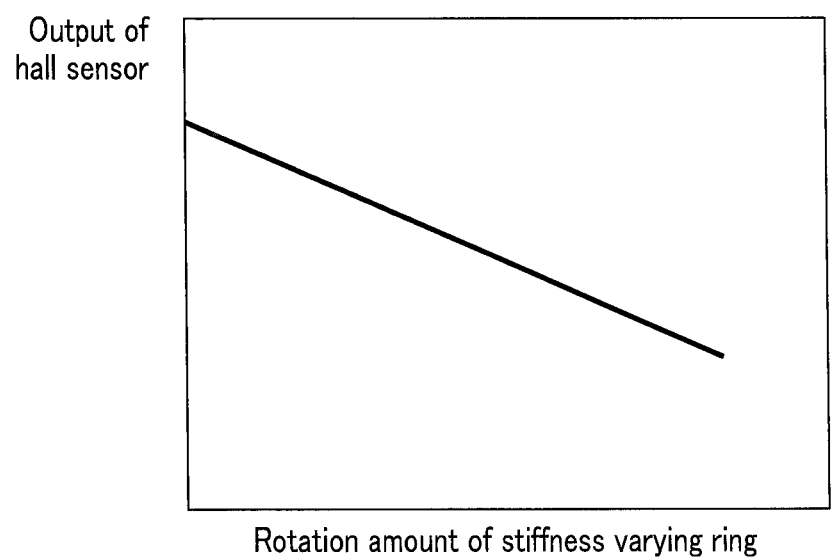
FIG. 6 is a graph representing the relationship between the rotation amount of a stiffness varying ring and the output value of a hall sensor.

When the stiffness varying ring 26 is rotated, the distance between the magnet 31 and the hall sensor 32 changes, and in accordance therewith, the magnitude of the magnetic flux detected by the hall sensor 32 changes. For example, assuming that the distance between the magnet 31 and the hall sensor 32 is closest to each other when the stiffness varying ring 26 is least rotated, the value of the output which the hall sensor 32 produces then is a maximum value. The output of the hall sensor 32 decreases in accordance with an increase in the distance between the magnet 31 and the hall sensor 32. Therefore, the relationship between the rotation amount of the stiffness varying ring 26 and the output of the hall sensor 32 can be shown as in FIG. 6. Therefore, by associating the rotation amount of the stiffness varying ring 26 and the degree of stiffness of the insertion section 10 with each other in advance, the degree of stiffness can be detected based on an output of the hall sensor 32.

Figure 7:
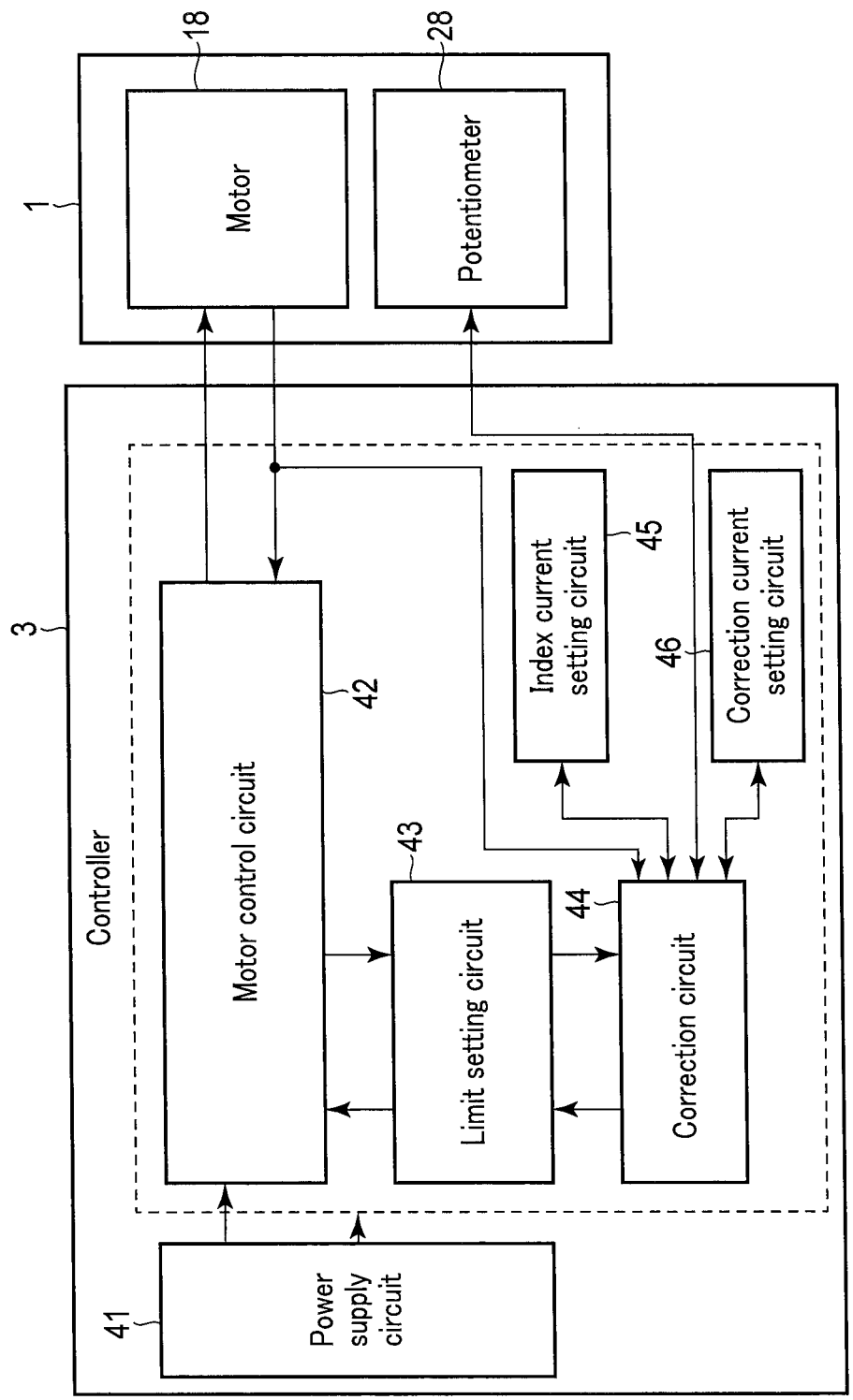
FIG. 7 is a block diagram illustrating the electric circuit configuration of a controller.

FIG. 7 is a block diagram illustrating the electric circuit configuration of the controller 13. In FIG. 7, the stiffness detector is made of the potentiometer 28. In place of this structure, the stiffness detector may be made of a combination of the magnet 31 and the hall sensor 32. In addition, the stiffness detector may be made of an encoder or the like which detects the rotation amount of the stiffness varying ring 26.

As shown in FIG. 7, the controller 13 includes a power supply circuit 41, a motor control circuit 42, a limit setting circuit 43, a correction circuit 44, an index current setting circuit 45, and a correction current setting circuit 46.

The power supply circuit 41 generates electric power for driving each block of the controller 13 and supplies the generated electric power to each block of the controller 13.

The motor control circuit 42 controls the driving of the motor 18 by controlling the driving electric power to be supplied to the motor 18 (for example, by controlling the magnitude of the current). The motor control circuit 42 controls the magnitude of the motor current supplied to the motor 18, such that the rotating speed of the spiral tube 14 becomes equal to a setting rotating speed (e.g., 30 rpm). For example, the motor control circuit 42 receives a rotation signal of the encoder provided for the motor 18 and determines the magnitude of the current to be supplied to the motor 18 such that the rotation signal indicates the setting rotating speed. Based on this control, the spiral tube 14 is rotated in the body cavity, and even if the torque of the spiral tube 14 varies, the rotating speed of the spiral tube 14 maintains a constant value.

When the torque limit state of the spiral tube 14 (actually the motor 18) is determined, the motor control circuit 42 stops power supply to the motor 18. The torque limit state is a state where the torque of the spiral tube 14 exceeds a predetermined upper limit value. To be more specific, the motor control circuit 42 compares a motor current, which is calculated from a rotation signal (corresponding to a torque) of the encoder provided for the motor 18, with a torque limit value, which is a threshold value set by the limit setting circuit 43. When the value of the motor current becomes equal to the torque limit value, the motor control circuit 42 stops the power supply to the motor 18.

The limit setting circuit 43 sets a torque limit value. The torque limit value is determined by adding a correction value to a predetermined reference torque limit value.

The correction circuit 44 reads an index current corresponding to the stiffness varying amount detected by the potentiometer 28 (i.e., the rotation amount of the stiffness varying ring 26) from the index current setting circuit 45, compares the read index current with a motor current obtained from the rotation signal of the encoder provided for the motor 18, and selects a correction current from the correction current setting circuit 46 based on the result of comparison.

The index current setting circuit 45 sets an index current. The index current is a threshold value used for determining whether or not the torque limit value should be corrected in accordance with the stiffness varying amount.

The correction current setting circuit 46 sets a correction current. The correction current is the value of a correction current used for correcting the torque limit value associated with the stiffness varying amount.

Figure 8:
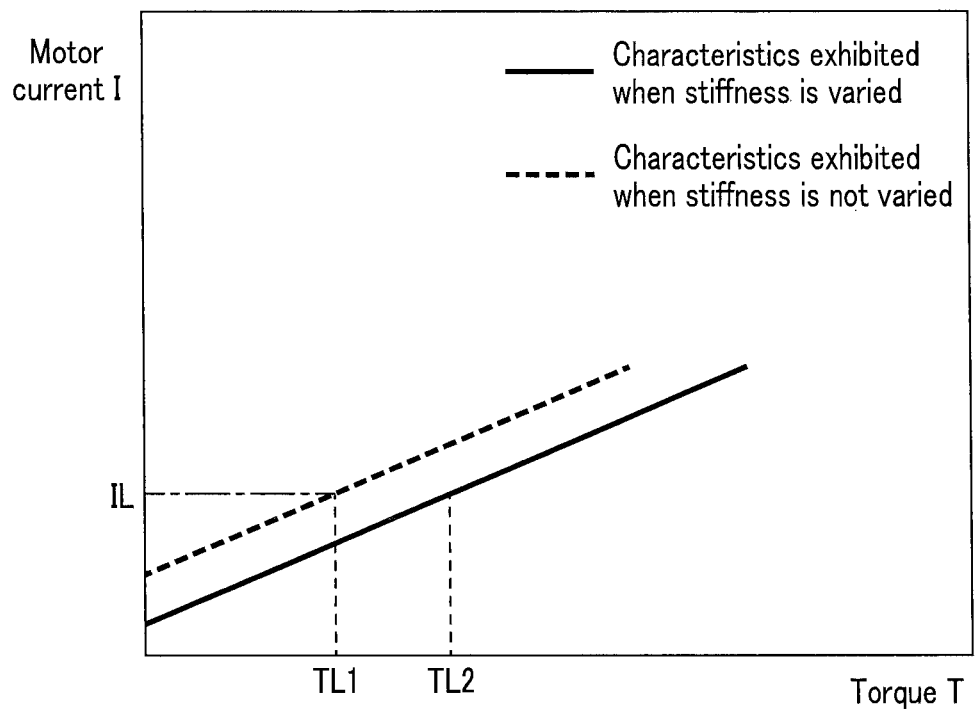
FIG. 8 is a first example of a graph representing the torque characteristics of a drive unit including a spiral tube.
Figure 9:
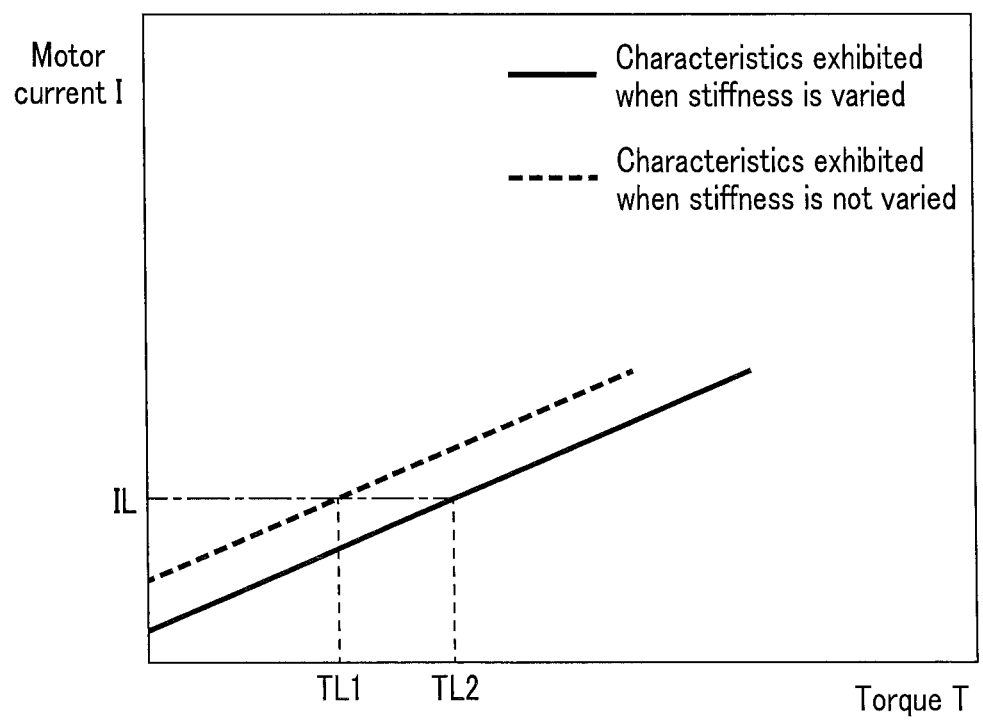
FIG. 9 is a second example of a graph representing the torque characteristics of a drive unit including a spiral tube.

A description will now be given of how the insertion device of the present embodiment corrects the torque limit value. FIGS. 8 and 9 are graphs representing the torque characteristics of the drive unit 15 including the spiral tube 14. FIG. 8 is a graph illustrating how the torque limit value is set in the state where the stiffness is not varied, and FIG. 9 is a graph illustrating how the torque limit value is set in the state where the stiffness is varied. In FIGS. 8 and 9, the broken lines indicate the state where the stiffness is not varied, and the solid lines indicate the state where the stiffness is varied.

FIG. 8 will be explained first. It is assumed that TL1 in FIG. 8 is the value of a torque that can be applied to the spiral tube 14 in the case where the stiffness is not varied. In this case, the motor 18 is controlled such that the torque of the spiral tube 14 does not exceed TL1. If the motor current obtained when the torque is TL1 is a torque limit value IL, the controller 13 performs control such that the value of the motor current does not exceed the torque limit value IL.

Where the stiffness is varied, the change amount of the motor current relative to the change amount of the torque decreases, compared with the case where the stiffness is not varied. Therefore, if the stiffness is varied and the motor 18 is controlled based on the torque limit value IL which is the same as the torque limit value in the case where the stiffness is not varied, the motor 18 stops when the torque of the spiral tube 14 becomes equal to TL2. In such a case, an excessive torque may be applied to the body cavity from the spiral tube 14.

It is assumed that TL2 in FIG. 9 is the value of a torque that can be applied to the spiral tube 14 in the case where the stiffness is varied. In this case, the motor 18 is controlled such that the torque of the spiral tube 14 does not exceed TL2. If the motor current obtained when the torque is TL2 is a torque limit value IL, the controller 13 performs control such that the value of the motor current does not exceed the torque limit value IL.

As mentioned above, where the stiffness is varied, the change amount of the motor current relative to the change amount of the torque decreases, compared with the case where the stiffness is not varied. Therefore, if the stiffness is not varied and the motor 18 is controlled based on the torque limit value IL which is the same as the torque limit value in the case where the stiffness is varied, the motor 18 stops before the torque of the spiral tube 14 becomes equal to TL1. In this case, a torque which would be effective in inserting the insertion section 10 is not generated.

As described above, it is desirable that the value of the motor current which should be used as a torque limit value is changed in accordance with whether or not the stiffness is varied. In order to determine a torque limit state based on the same torque between the case where the stiffness is varied and the case where the stiffness is not varied, the difference $\Delta i$ between the motor current IL1 corresponding to torque value TL1 (which can be applied to the spiral tube 14 when the stiffness is not varied) and the motor current IL2 corresponding to torque value TL2 (which can be applied to the spiral tube 14 when the stiffness is varied) should be added to the reference torque limit value.

A specific correction method will be described. First of all, a reference value of a torque limit value is determined. It is assumed that the reference value of the torque limit value is the value of a motor current corresponding to the torque that can be applied to the spiral tube 14 in the case where the insertion section 10 does not bend and the stiffness thereof is not varied. In the following, the reference value of the torque limit value will be referred to as torque limit value ILf.

Even if a motor current of the same magnitude is kept supplied to the motor, the torque applied to the spiral tube 14 may vary, depending upon the bending state of the insertion section 10. The torque applied to the spiral tube 14 may also vary, depending upon the way in which the stiffness is varied. In the present embodiment, therefore, the index current and correction current corresponding to the typical state of the insertion section 10 are read and used, in accordance with the stiffness varying amount. Accordingly, the torque limit value can be corrected in consideration of not only the stiffness varying amount but also the bending state of the insertion section 10.

Figure 10:
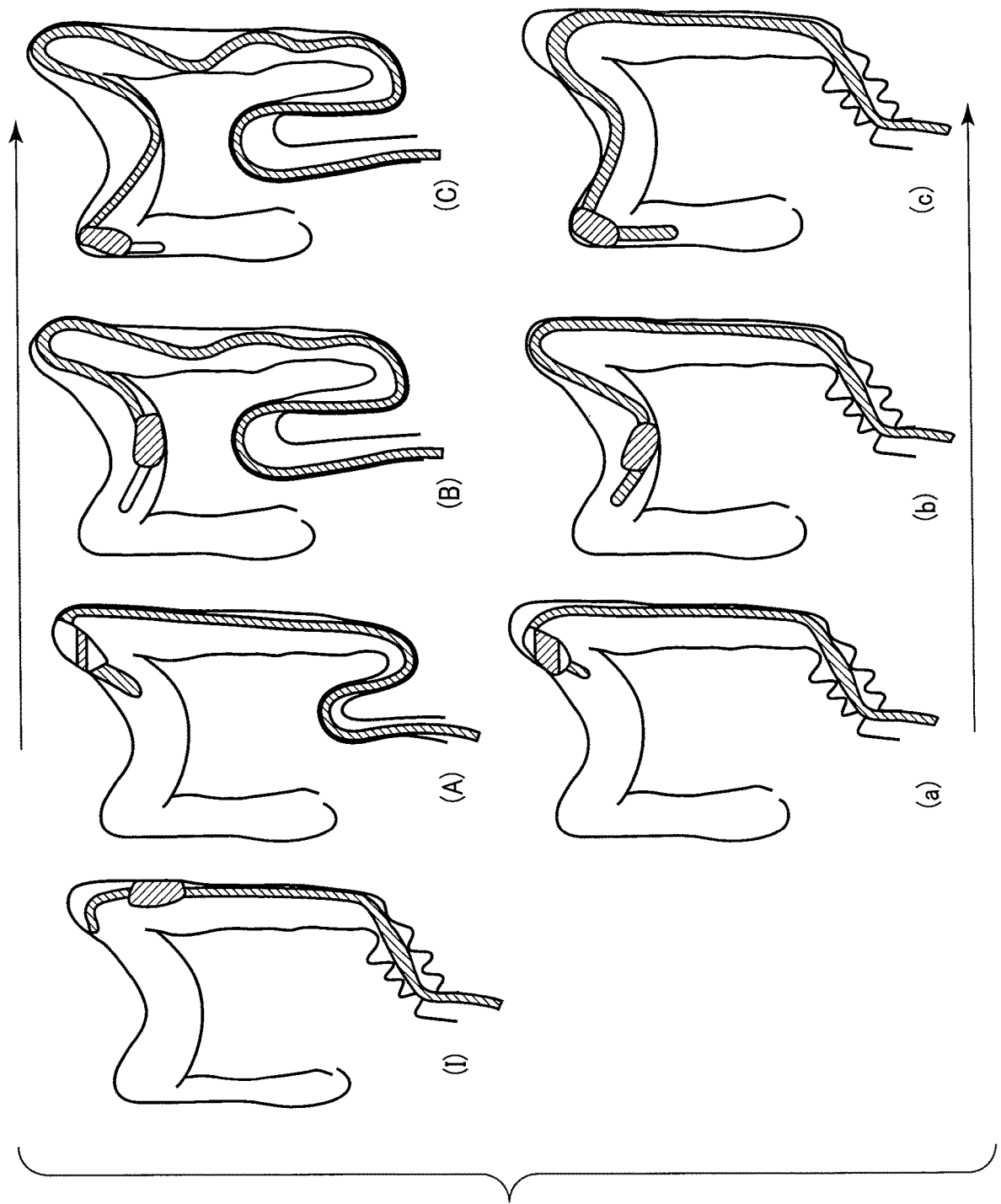
FIG. 10 shows diagrams illustrating how stiffness variation is used when an insertion section is inserted into a deep portion of the large intestine.

FIG. 10 shows diagrams illustrating how variable stiffness is used in the case where the insertion section 10 is inserted into a deep portion of the large intestine, the case being a typical example in which the spiral tube 14 is used. In FIG. 10, "I" shows how the insertion section 10 is when it is inserted to the splenic flexure. In "I" of FIG. 10, it is assumed that the insertion section 10 is inserted in the state where the sigmoid colon is folded. In FIG. 10, "A", "B" and "C" show how the insertion section is inserted to respective insertion points of the large intestine, without the stiffness of the insertion section being varied, and "a", "b" and "c" show how the insertion section is inserted to respective insertion points of the large intestine, with the stiffness of the insertion section being varied. In FIG. 10, "A" and "a" show the states where the insertion section 10 passes over the splenic flexure. In FIG. 10, "B" and "b" show the states where the insertion section 10 passes over the sag of the transverse colon. In FIG. 10, "C" and "c" show the states where the insertion section 10 passes over the hepatic flexure.

When the insertion section 10 is inserted into the large intestine, it passes the sigmoid colon in the folded state and reaches the splenic flexure, as shown in "I" in FIG. 10.

Where the insertion section 10 is made to pass over the splenic flexure without using the stiffness variation, the operator performs an operation for rotating the spiral tube 14. In this case, the insertion section passes over the splenic flexure but the sigmoid colon in the folded state is stretched, as shown in "A" of FIG. 10. Where the insertion section 10 is made to pass over the splenic flexure, using the stiffness variation, the operator performs an operation for rotating the spiral tube 14, and simultaneously rotates the stiffness varying ring 26 so that the insertion section 10 can have a certain degree of stiffness (the amount by which the stiffness varying ring 26 is rotated then will be referred to as rotation amount 1). Since the insertion section 10 hardly bends then, the sigmoid colon is kept in the folded state and the insertion section 10 passes over the splenic flexure, as shown in "a" of FIG. 10.

Subsequently, where the insertion section 10 is made to pass over the sag of the transverse colon without using the stiffness variation, the operator continues to perform an operation for rotating the spiral tube 14. Since the insertion length inevitably increases when the insertion section 10 is in the sag of the transverse colon, a torque may not be transmitted reliably to the distal end of the insertion section 10. As shown in "B" of FIG. 10, the insertion section 10 in the transverse colon bends, and the insertion section 10 in the sigmoid colon also bends in such a manner as to push up the sigmoid colon. On the other hands, where the insertion section 10 is made to pass over the splenic flexure, using the stiffness variation, the operator performs an operation for rotating the spiral tube 14, and simultaneously rotates the stiffness varying ring 26 further so that the insertion section 10 can have a higher degree of stiffness (the amount by which the stiffness varying ring 26 is rotated then will be referred to as rotation amount 2, which is larger than rotation amount 1). Since the bend of the insertion section 10 lessens, the insertion section 10 can be inserted, with the sigmoid colon kept in the folded state, as shown in "b" of FIG. 10.

Subsequently, where the insertion section 10 is made to pass over the hepatic flexure, the operator continues to perform an operation for rotating the spiral tube 14. Since the insertion length increases further when the insertion section 10 is in the hepatic flexure, the transmission characteristic of a torque to the distal end of the insertion section 10 worsens. As shown in "C" of FIG. 10, therefore, the insertion section 10 in the descending colon has an increased bend. On the other hands, where the insertion section 10 is made to pass over the hepatic flexure, using the stiffness variation, the operator performs an operation for rotating the spiral tube 14, and simultaneously rotates the stiffness varying ring 26 further so that the insertion section 10 can have a further degree of stiffness (the amount by which the stiffness varying ring 26 is rotated then will be referred to as rotation amount 3, which is larger than rotation amount 2). Since the bend of the insertion section 10 lessens further, the insertion section 10 passes over the hepatic flexure, as shown in "c" of FIG. 10.

Figures 11, 12:
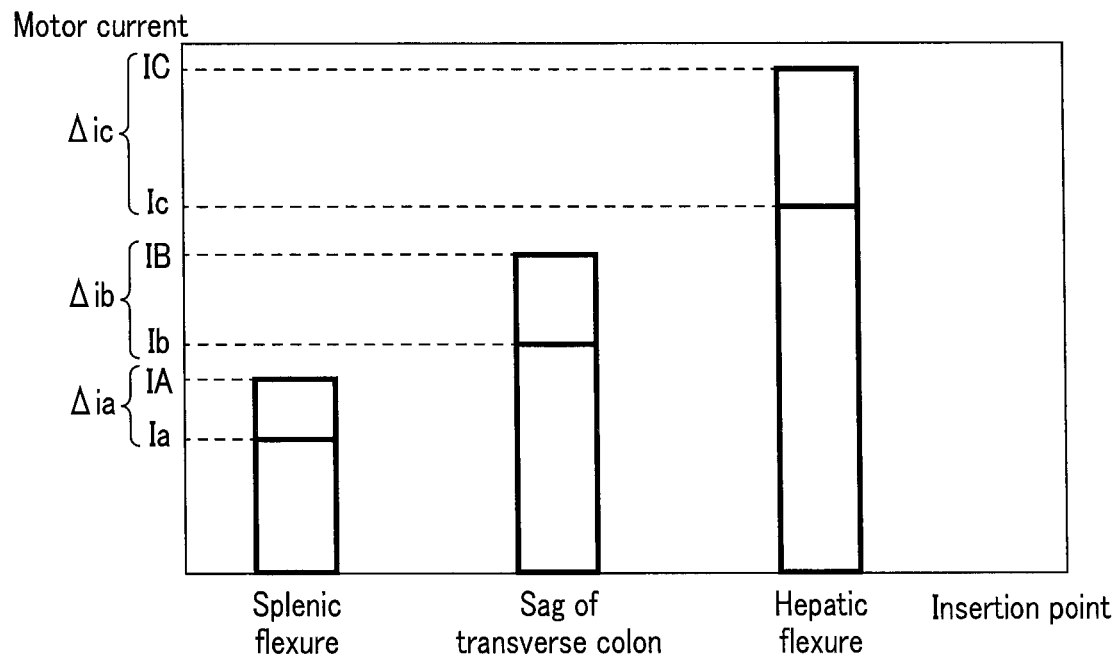
FIG. 11 illustrates how the use/non-use of the stiffness variation at each of the insertion points depicted in FIG. 10 is related to the motor current for obtaining the torque necessary for insertion.
FIG. 12 illustrates an example of the correspondence among a stiffness varying amount (the output of a potentiometer), an index current and a correction current.

As described above, when the insertion section 10 is inserted to a deep portion of the large intestine, the stiffness is varied usually in three steps. In the present embodiment, therefore, a correction current is selected from the correction currents corresponding to the three step of the stiffness variation. FIG. 11 illustrates how the use/non-use of the variable stiffness at each of the insertion points depicted in FIG. 10 is related to the motor current for obtaining the torque necessary for insertion. In FIG. 11, the abscissa axis represents insertion points. The ordinate axis represents values of the motor current. "IA" on the ordinate axis represents how the value of a motor current is when the insertion point is in the splenic flexure and the stiffness variation is not used. "Ia" represents how the value of the motor current is when the insertion point is in the splenic flexure and the stiffness variation is used. "IB" represents how the value of the motor current is when the insertion point is in the sag of the transverse colon and the stiffness variation is not used. "Ib" represents how the value of the motor current is when the insertion point is in the sag of the transverse colon and the stiffness variation is used. "IC" represents how the value of the motor current is when the insertion point is in the hepatic flexure and the stiffness variation is not used. "Ic" represents how the value of the motor current is when the insertion point is in the hepatic flexure and the stiffness variation is used. $\Delta ia$ is the difference between IA and Ia, namely, a correction current to be applied when the insertion point is in the splenic flexure. $\Delta ib$ is the difference between IB and Ib, namely, a correction current to be applied when the insertion point is in the sag of the transverse colon. $\Delta ic$ is the difference between IC and Ic, namely, a correction current to be applied when the insertion point is in the hepatic flexure.

As shown in FIG. 11, the motor current necessary for insertion increases in accordance with an increase in the insertion length (in accordance with the depth of the insertion point in the large intestine). Where the stiffness variation is not used, the magnitude of the motor current necessary for insertion increases. In addition, the magnitude of the motor current necessary for insertion decreases in accordance with an increase of the stiffness variation. The index current and the correction current are expressed as numerical values, based on the relationship shown in FIG. 11.

FIG. 12 illustrates an example of the correspondence among the stiffness varying amount (the output of the potentiometer 28), the index current and the correction current. Of the values shown in FIG. 12, the output value of the potentiometer 28 and the value of the index current are stored in the index current setting circuit 45 in association with each other. Motor currents IA, IB and IC are used as the values of index currents. These index currents are compared with motor currents calculated based on rotation signals supplied from the encoder. Based on this comparison, it can be determined whether the state of the insertion section 10 is the state shown in "a", "b" or "c" of FIG. 10. Of the values shown in FIG. 12, the output value of the potentiometer 28 and the value of the correction current are stored in the correction current setting circuit 46 in association with each other. $\Delta ia$, $\Delta ib$ and $\Delta ic$ are used as values of the correction currents. The torque limit values can be corrected by adding these values of the correction currents to the reference torque limit value ILf.

FIG. 13 is a flowchart illustrating torque limit processing. The processing shown in FIG. 13 is started, for example, when one of the forward switch 11c, backward switch 11d, pedal 130a and pedal 130b is operated after the controller 13 is turned on. For the sake of simplicity, the rotation amount of the stiffness varying ring 26 is limited to rotation amount 1 (the output value of the potentiometer 28 is Ra), rotation amount 2 (the output value of the potentiometer 28 is Rb) or rotation amount 3 (the output value of the potentiometer 28 is Rc). It should be noted that Rc>Rb>Ra.

In step S1, the motor control circuit 42 of the controller 13 starts power supply to the motor 18 such that the motor 18 can be rotated in accordance with the operation of the forward switch 11c, backward switch 11d, pedal 130a or pedal 130b. The spiral tube 14 is rotated in accordance with the rotation of the motor 18.

In step S2, the correction circuit 44 of the controller 13 determines whether or not the stiffness variation is used. In step S2, the use of the stiffness variation is determined where a signal from the potentiometer 28 is supplied. If the use of the stiffness variation is determined in step S2, the processing advances to step S3. If the non-use of the stiffness variation is determined in step S2, the processing advances to step S10.

In step S3, the correction circuit 44 checks the value of the potentiometer 28. If the value of the potentiometer 28 is Ra, the processing advances to step S4. If the value of the potentiometer 28 is Rb, the processing advances to step S6. If the value of the potentiometer 28 is Rc, the processing advances to step S8.

In step S4, the correction circuit 44 determines whether the value of the motor current Im calculated based on a rotation signal from the encoder is equal to index current IA or more. If it is determined in step S4 that the value of the motor current Im is equal to index current IA or more, the processing advances to step S5. If it is determined in step S4 that the value of the motor current Im is less than index current IA, the processing advances to step S11.

Where the value of the potentiometer 28 is Ra and the value of the motor current Im is equal to IA or more, the state shown in "a" of FIG. 10 is assumed. In this case, the torque limit value has to be corrected. In step S5, the correction circuit 44 reads correction current $\Delta ia$ from the correction current setting circuit 46 and supplies the read correction current $\Delta ia$ to the limit setting circuit 43. The limit setting circuit 43 corrects torque limit value IL by adding correction current $\Delta ia$ to reference value ILf of the torque limit value. Subsequently, the flow advances to step S11.

In step S6, the correction circuit 44 determines whether the motor current Im calculated based on a rotation signal from the encoder is equal to index current IB or more. If it is determined in step S6 that the value of the motor current Im is equal to index current IB or more, the processing advances to step S7. If it is determined in step S6 that the value of the motor current Im is less than index current IB, the processing advances to step S4. This indicates the case where the stiffness variation is used excessively in the state shown in "a" of FIG. 10.

Where the value of the potentiometer 28 is Rb and the value of the motor current Im is equal to IB or more, the state shown in "b" of FIG. 10 is assumed. In this case, the torque limit value has to be corrected. In step S7, the correction circuit 44 reads correction current $\Delta ib$ from the correction current setting circuit 46 and supplies the read correction current $\Delta ib$ to the limit setting circuit 43. The limit setting circuit 43 corrects torque limit value IL by adding correction current $\Delta ib$ to reference value ILf of the torque limit value. Subsequently, the processing advances to step S11.

In step S8, the correction circuit 44 determines whether the value of the motor current Im calculated based on a rotation signal from the encoder is equal to index current IC or more. If it is determined in step S8 that the value of the motor current Im is equal to index current IC or more, the processing advances to step S9. If it is determined in step S8 that the value of the motor current Im is less than index current IC, the processing advances to step S6. This indicates the case where the stiffness variation is used excessively in the state shown in "a" or "b" of FIG. 10.

Where the value of the potentiometer 28 is Rc and the value of the motor current Im is equal to IC or more, the state shown in "c" of FIG. 10 is assumed. In this case, the torque limit value has to be corrected. In step S9, the correction circuit 44 reads correction current $\Delta ic$ from the correction current setting circuit 46 and supplies the read correction current $\Delta ic$ to the limit setting circuit 43. The limit setting circuit 43 corrects torque limit value IL by adding correction current $\Delta ic$ to reference value ILf of the torque limit value. Subsequently, the processing advances to step S11.

In step S10, the correction circuit 44 sets torque limit value IL as reference value ILf. Since the stiffness variation is not used, the torque limit value IL is changed back to reference value ILf. Subsequently, the processing advances to step S11.

In step S11, the motor control circuit 42 determines whether the value of the motor current Im calculated based on a rotation signal from the encoder is equal to torque limit value IL set in the limit setting circuit 43 or more. If it is determined in step S11 that the value of the motor current Im is equal to torque limit value IL set in the limit setting circuit 43 or more, then the processing advances to step S12. If it is determined in step S11 that the value of the motor current Im is less than torque limit value IL set in the limit setting circuit 43, then the processing advances to step S13.

In step S12, the motor control circuit 42 stops the power supply to the motor 18. Because of this, the generation of an excessive torque applied to the spiral tube 14 is suppressed. After the torque limit function is performed, the motor is rotated again when one of the forward switch 11c, backward switch 11d, pedal 130a and pedal 130b is operated. Subsequently, the processing advances to step S13.

In step S13, the motor control circuit 42 determines whether or not the controller 13 is turned off. If it is determined in step S13 that the controller 13 is not OFF, the processing returns to step S2. If it is determined in step S13 that the controller 13 is OFF, the processing shown in FIG. 13 is ended.

As described above, the present embodiment provides an endoscope including a variable stiffness section 22, and the driving of the motor 18 is controlled in accordance with the stiffness varying amount of the variable stiffness section 22. Owing to this, the torque limit function is properly performed, and yet the motor 18 can be controlled based on an optimal motor current determined in accordance with the stiffness varying amount. That is, the torque of the spiral tube 14 can be varied not only by operating the foot switch but also by rotating the stiffness varying ring 26.

In the embodiment described above, the rotating body used for advancing or retreating the insertion section 10 of the endoscope 1 (an insertion device) is the spiral tube 14. This is not restrictive, and the technology of the present embodiment is applicable to various types of insertion device in which the insertion section 10 is advanced or retreated by means of a rotating body.

The present invention has been described based on one embodiment, but is not limited to the above-described embodiment. Needless to say, various modifications or applications can be made without departing from the spirit and scope of the present invention. The operations described above do not have to be performed in the order mentioned in the flowchart.

The operations described in relation to the above embodiment may be stored in the form of programs executable by a CPU (which is a computer) or the like. The programs can be stored in storage mediums of external storage devices, such as a memory card, a magnetic disk, an optical disk or a semiconductor memory, and distributed. The CPU or the like reads the programs from a storage medium of an external storage device, and the operations can be executed and controlled based on the read programs.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
    a thin and elongated insertion section;
    a rotating body which is rotated to advance or retreat the insertion section;
    a motor which supplies a driving force to the rotating body;
    a variable stiffness section provided for the insertion section, the variable stiffness section including a wire configured to be pushed or pulled to vary a stiffness of the insertion section;
    a stiffness sensor which detects the stiffness of the insertion section varied by the variable stiffness section;
    a controller which controls the motor in accordance with the stiffness of the insertion section detected by the stiffness sensor; and
    a drive shaft which is provided in the insertion section and transmits the driving force from the motor to the rotating body,
    wherein the controller corrects a torque limit value, which corresponds to an upper limit value of a torque of the rotating body, in accordance with the stiffness of the insertion section detected by the stiffness sensor, and controls the motor in accordance with the corrected torque limit value.

2. The insertion device according to claim 1, wherein the controller corrects the torque limit value such that the torque limit value increases in accordance with an increase in the stiffness of the insertion section detected by the stiffness sensor.

3. The insertion device according to claim 1, further comprising:
    an operation unit which receives an operation causing the variable stiffness section to vary the stiffness of the insertion section,
    wherein the variable stiffness section varies the stiffness of the insertion section in accordance with an operation amount of the operation unit.

4. The insertion device according to claim 1, wherein the controller stops the motor when a torque of the motor exceeds the corrected torque limit value.

* * * * *